US008611640B2

(12) United States Patent
Yamashita et al.

(10) Patent No.: US 8,611,640 B2
(45) Date of Patent: Dec. 17, 2013

(54) INSPECTION APPARATUS AND INSPECTION METHOD

(71) Applicant: Hitachi High-Tecnologies Corporation, Tokyo (JP)

(72) Inventors: Hiroyuki Yamashita, Fujioka (JP); Norio Sakaiya, Hitachinaka (JP); Kei Shimura, Mito (JP); Masaaki Ito, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/692,732

(22) Filed: Dec. 3, 2012

(65) Prior Publication Data

US 2013/0100446 A1 Apr. 25, 2013

Related U.S. Application Data

(63) Continuation of application No. 12/338,528, filed on Dec. 18, 2008, now Pat. No. 8,351,683.

(30) Foreign Application Priority Data

Dec. 25, 2007 (JP) ................................. 2007-331316
Mar. 12, 2008 (JP) ................................. 2008-062840

(51) Int. Cl.
*G06T 11/20* (2006.01)
*G01N 21/88* (2006.01)

(52) U.S. Cl.
USPC ........................................................ 382/149

(58) Field of Classification Search
USPC ........ 382/128–154; 356/237.1–237.5; 362/29
See application file for complete search history.

(56) References Cited

U.S. PATENT DOCUMENTS

| 4,521,075 A | * | 6/1985 | Obenschain et al. ......... 359/569 |
| 4,619,508 A | * | 10/1986 | Shibuya et al. ............... 353/122 |
| 7,046,353 B2 | | 5/2006 | Isozaki et al. |
| 7,424,146 B2 | | 9/2008 | Honda et al. |

(Continued)

FOREIGN PATENT DOCUMENTS

| JP | 62-89336 A | 4/1987 |
| JP | 1-117024 A | 5/1989 |

(Continued)

OTHER PUBLICATIONS

Japanese Notification of Reasons for Refusal, w/ English translation thereof, issued in Japanese Patent Application No. JP 2008-062840 dated Jun. 1, 2010.

(Continued)

*Primary Examiner* — Hoa Pham
(74) *Attorney, Agent, or Firm* — McDermott Will & Emery LLP

(57) ABSTRACT

The invention is directed to find a false defect from defect candidates and obtain a threshold with which the false defect can be eliminated by the smallest number of review times. Defect candidates are reviewed and selected as a defect or a false defect. By deleting a defect candidate having a characteristic quantity equal to or less than that of the false defect from a map or displaying it in another sign, the false defect can be determined visually. Since the defect candidate having the characteristic quantity equal to or less than that of the selected false defect is deleted from the map or displayed in another sign, the defect candidates unnecessary to set a threshold are not reviewed. The number of defect candidates to be reviewed can be largely reduced as compared with that in the conventional technique. Further, by repeating the above work, the threshold is automatically calculated, and an inspection result map with the threshold is displayed, so that a re-inspection is unnecessary.

6 Claims, 13 Drawing Sheets

(56) References Cited

U.S. PATENT DOCUMENTS

| | | |
|---|---|---|
| 7,508,973 B2 | 3/2009 | Okabe et al. |
| 7,586,959 B2 * | 9/2009 | Korngut et al. ................. 372/25 |
| 7,720,275 B2 | 5/2010 | Shibuya et al. |
| 7,734,082 B2 | 6/2010 | Honda et al. |
| 2005/0147287 A1 | 7/2005 | Sakai et al. |
| 2005/0264797 A1 | 12/2005 | Nakano et al. |
| 2006/0133660 A1 | 6/2006 | Ogi et al. |
| 2006/0163503 A1 * | 7/2006 | Urano et al. ............. 250/559.42 |
| 2006/0171138 A1 * | 8/2006 | Muramatsu et al. ............ 362/29 |
| 2007/0121106 A1 | 5/2007 | Shibata et al. |
| 2007/0177136 A1 * | 8/2007 | Nakano et al. ............ 356/237.2 |
| 2008/0015802 A1 | 1/2008 | Urano et al. |
| 2009/0148031 A1 | 6/2009 | Fukami |
| 2009/0161943 A1 | 6/2009 | Yamashita et al. |
| 2010/0106443 A1 | 4/2010 | Shimura et al. |
| 2010/0208249 A1 | 8/2010 | Shibata et al. |
| 2010/0246933 A9 | 9/2010 | Hiroi et el. |

FOREIGN PATENT DOCUMENTS

| | | | |
|---|---|---|---|
| JP | 8-210989 A | 8/1996 |
| JP | 10-010522 A | 1/1998 |
| JP | 2000-105203 A | 4/2000 |
| JP | 2001-077165 A | 3/2001 |
| JP | 2003-166947 A | 6/2003 |
| JP | 2004-177139 A | 6/2004 |
| JP | 2005-017159 A | 1/2005 |
| JP | 2005-337851 A | 12/2005 |
| JP | 2006-170809 A | 6/2006 |
| JP | 2007-085958 A | 4/2007 |
| JP | 2007-101401 A | 4/2007 |

OTHER PUBLICATIONS

Japanese of Action, with English translation, issued in Japanese Patent Application No. 2007-331316, dated Feb. 28, 2012.

Japanese Office Action, and English translation thereof, issued in Japanese Patent Application No. 2010-171540 dated Jun. 19, 2012.

Japanese Office Action, and English translation thereof, issued in Japanese Patent Application No. 2007-331316 dated Oct. 9, 2012.

Entire Prosecution of U.S. Appl. No. 13/338,528 to Yamashita et al. entitled "Inspection Apparatus and Inspection Method".

* cited by examiner

Selection of false defects

Selection of false defects

INSPECTION APPARATUS AND INSPECTION METHOD

The present application is a Continuation of U.S. application Ser. No. 12/338,528 filed on Dec. 18, 2008, now U.S. Pat. No. 8,351,683, which claims priority from Japanese application Nos. JP 2008-062840 filed on Mar. 12, 2008 and JP 2007-331316 filed on Dec. 25, 2007, the entire contents of each of which are hereby incorporated by reference into this application.

BACKGROUND OF THE INVENTION

1. Field of the Invention

The invention relates to an inspection apparatus and an inspection method for detecting particles, flaw, defect, dirt, and the like (hereinbelow, generically called defect) existing in the surface of an object to be inspected such as a semiconductor wafer.

The invention relates to a defect inspection method and a defect inspection apparatus for detecting a defect such as a particle or deformation in a pattern in a manufacturing process of a semiconductor device, a liquid crystal display device, a printed board, or the like.

2. Description of the Related Art

For example, an inspection apparatus for detecting a defect in a semiconductor wafer detects a defect existing in the surface of a wafer by irradiating the surface of the wafer with inspection light such as a laser beam and detecting reflection light or scattered light generated on the surface of the wafer.

In the inspection apparatus of this kind, in the case where a pattern for constructing a chip is formed in the surface of a wafer, usually, an image signal is generated on the basis of the intensity of the detected reflection light or scattered light. An image signal in an inspection area (inspection chip or inspection shot) is compared with an image signal in a reference area (reference chip or reference shot), and a part where the difference between the signals is equal to or larger than a threshold is determined as a particle. As the reference area, an area adjacent to the inspection area (adjacent chip or adjacent shot) or a prepared conforming area (conforming chip or conforming shot) is used.

In the inspection apparatus, inspection condition data corresponding to the kinds of wafers and inspection processes is necessary. It takes long time to generate the data. It takes the longest time for setting a threshold in generation of the inspection condition data.

A threshold is set as follows. First, an inspection is conducted using standard inspection condition data. A detected defect candidate is observed by a microscope, and whether the defect candidate is a defect or a false defect is determined. This work will be called a review hereinbelow. When the number of defect candidates is large, the number of defect candidates to be reviewed and the kinds of defect candidates vary depending on the empirical values of users. Therefore, if a threshold with which all of false defects can be deleted is not found from the defect candidates, even if the threshold is changed and a re-inspection is executed, the false defects cannot be deleted, and the review and the re-inspection are repeated a few times.

Japanese Patent Application Laid-Open (JP-A) No. 2004-177139 describes a method of inputting a result of determination of whether a defect candidate is a defect or a false defect, displaying the defect and the false defect on a defect characteristic quantity distribution display unit, and calculating a change parameter from the distribution result.

In a semiconductor manufacturing process, when a particle exists on a semiconductor substrate (wafer), it causes a defect such as insufficient insulation of a wire or a short-circuit. As a pattern on a semiconductor device is becoming finer, when a small particle exists in the semiconductor substrate, it causes insufficient insulation of a capacitor or defect in gate oxides, etc.

Similarly, also in a liquid crystal display device manufacturing process, when a particle exists on a pattern or a defect occurs in the shape of a pattern, the display device cannot be used. Also in a process of manufacturing a printed board, existence of a particle causes short-circuiting of a pattern and poor connection.

One of conventional techniques for detecting a particle on a substrate is disclosed in JP-A No. 62-89336. In the technique, a semiconductor substrate is irradiated with an s-polarized laser beam, scattered light from a particle generated when a particle is adhered on the semiconductor substrate is detected and compared with an inspection result of the same kind of a semiconductor substrate inspected just before, thereby eliminating a false defect caused by a pattern and enabling a high-sensitive high-reliable particle and defect inspection to be performed.

As the technique of detecting the particle, there is a known method of irradiating a wafer with coherent light, eliminating light emitted from a repetitive pattern on the wafer with a spatial filter, and emphasizing and detecting non-repeated defects and particles.

JP-A No. 1-117024 discloses a particle inspection apparatus for irradiating a circuit pattern formed on a wafer with illumination light in a direction tilted with respect to a main straight line group of the circuit pattern by 45 degrees and preventing diffracted light from the main straight line group from entering the aperture of an objective lens in a detection optical system. In the publication, it is also described that light from straight line groups other than the main straight line group is blocked with a spatial filter.

JP-A Nos. 8-210989 and 2005-337851 describe a method of reducing noise components in an image and improving inspection sensitivity in a non-repetitive pattern portion by dropping coherency of the illumination.

JP-A No. 2000-105203 discloses a conventional technique on an apparatus and method for detecting a defect such as a particle.

SUMMARY OF THE INVENTION

To shorten the time of setting a threshold, it is a problem to efficiently find a false defect from defect candidates and to obtain a threshold with which false defects can be deleted by the smallest number of review times.

An object of the invention is to provide an inspection apparatus and an inspection method solving the problem and capable of reducing inspection condition generation time.

To achieve the object, as an feature of the invention, when an arbitrary defect candidate is selected from a defect candidate group, the defect candidate group is classified to a defect candidate group having a characteristic quantity equal to or less than that of the selected defect candidate and a defect candidate group having a characteristic quantity larger than that of the selected defect candidate. On the basis of the classification result, a threshold for determining whether there is a defect in the surface of an object to be inspected or not is calculated.

As another feature, when a defect candidate is selected, the threshold is updated.

Further, as another feature, each time a defect candidate is selected, the threshold is displayed. Each time a defect candidate is selected, a defect candidate group is displayed as a first defect candidate group and a second defect candidate group or displayed while deleting a defect candidate group having a characteristic quantity equal to or less than that of the defect candidate.

According to the invention, the inspection condition data generation time can be shortened.

In a process of manufacturing a semiconductor and a liquid crystal display device, as a pattern is becoming finer, it is becoming more important to detect a defect caused by a defective shape in the pattern such as a short-circuit and a disconnection.

However, in the conventional technique, it is difficult to detect a short-circuit in a pattern at the bottom between a plurality of wires arranged in parallel. Specifically, even with a combination of the conventionally-used s-polarization illumination and the method of emitting light in a direction tilted with respect to a main straight line group by 45 degrees and preventing diffracted light from entering a detection optical system disclosed in JP-A No. 1-117024, it is difficult to detect the short-circuit in a pattern.

Another object of the invention is to realize a defect inspection method and apparatus having improved sensitivity of an inspection on a short-circuit at the bottom between neighboring wires and capable of detecting even a pattern short-circuit at the bottom between a plurality of wires arranged in parallel in a finely formed pattern.

To achieve the object, the invention is constructed as follows.

In a defect inspection method and apparatus for irradiating an object to be inspected with illumination light from a direction tilted only by a predetermined angle, detecting reflection light by a detection optical system, and detecting a particle or a pattern defect in the object to be inspected, polarized light in a direction between p-polarized light and s-polarized light, in which reflection light scattered from a particle in the object to be inspected or a pattern defect is the largest is calculated on the basis of a predetermined incident angle of the illumination light, and the object to be inspected is irradiated with the illumination light in the calculated polarization state.

In a defect inspection method and apparatus for irradiating an object to be inspected with coherent light from a light source, detecting scattered reflection light, processing an obtained image, and detecting a particle or a pattern defect in the object to be inspected, linearly-polarized light or elliptically-polarized light outputted from the coherent light source is allowed to pass through an optical element that disturbs its polarization state, and the object to be inspected is irradiated with light in different polarization states.

In a defect inspection method and apparatus for condensing output light from a coherent light source, irradiating an object to be inspected with the output light, detecting scattered reflection light, processing an obtained image, and detecting a particle or a pattern defect in the object to be inspected, linearly-polarized light or elliptically-polarized light outputted from the coherent light source is allowed to pass through an optical element that gives different optical path lengths to a plurality of slit-like regions the light enters, and the passed light is spatially divided into two groups. One of polarization states is converted so as to be orthogonal to the other polarization state, and the object to be inspected is irradiated with the resultant light.

According to the invention, a defect inspection method and apparatus having improved sensitivity of an inspection on a short-circuit at the bottom between neighboring wires and capable of detecting even a pattern short-circuit at the bottom between a plurality of wires arranged in parallel in a finely formed pattern can be realized.

DESCRIPTION OF REFERENCE NUMERALS

Figure 1:
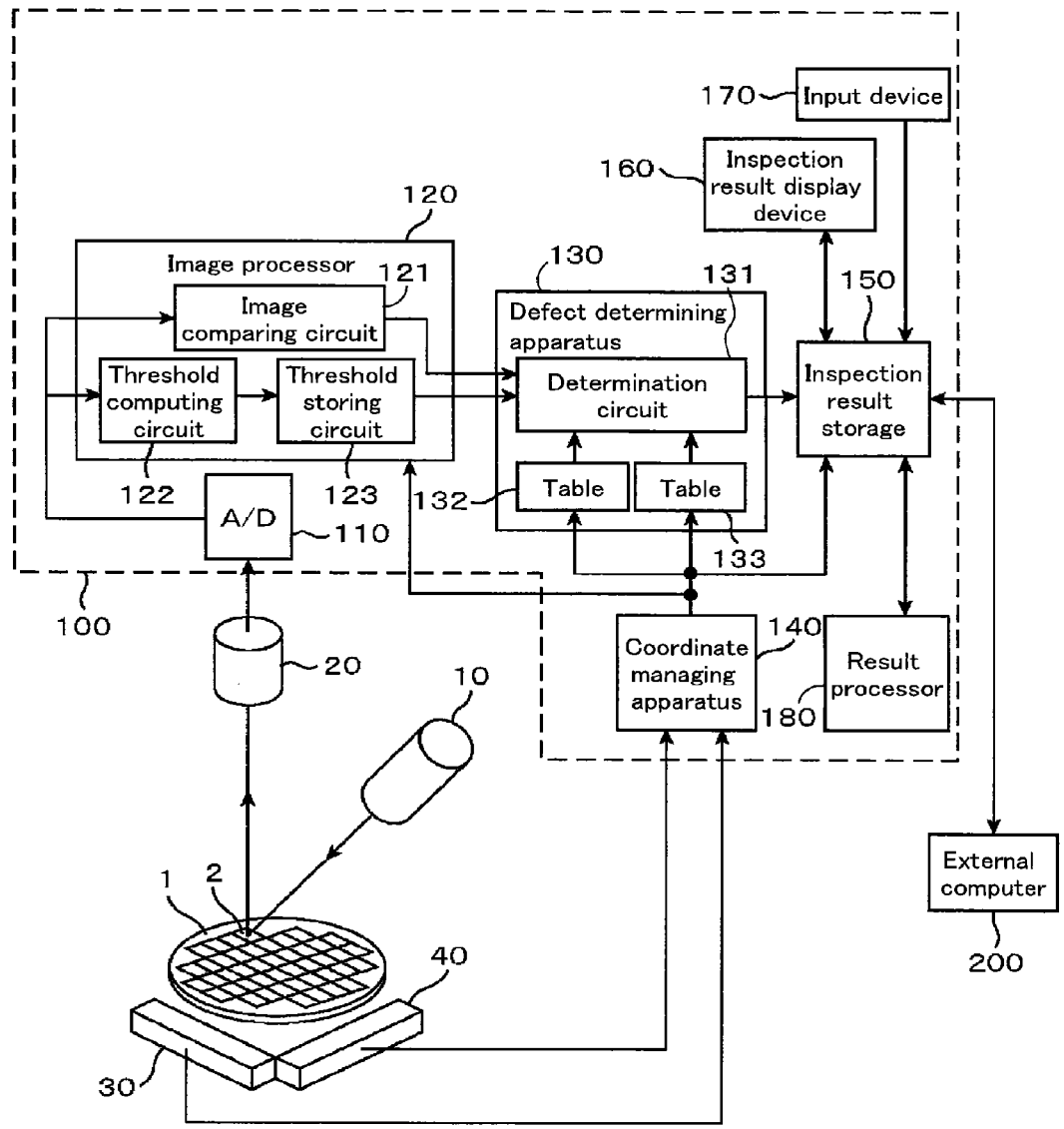
FIG. 1 is a schematic diagram of an inspection apparatus as a first embodiment of the invention.

1 wafer
10 illuminating means
20 detecting means
100 processor
120 image processor
121 image comparing circuit
122 threshold computing circuit
123 threshold storing circuit
130 defect determining apparatus
131 determination circuit
132, 133 coefficient tables
140 coordinate managing apparatus
150 inspection result storage
160 inspection result display device
170 input device
180 result processor 200 external computer
201 light source
210 polarization light adjuster
213 half-wavelength plate
215 quarter-wavelength plate
220 beam expander
230 lens
240 elevation angle switching mirror
300 light source
310 depolarizer
320 beam expander
330, 370 multiple glass block elements
340 cylindrical lens
350, 360 half-wavelength plates
801 object to be inspected (sample, substrate, and wafer)
802 illumination light
803 illumination optical system
804, 805 inspection optical systems
806, 807 sensors
810 illuminating system
815 stage
816 image processor
817 mechanism controller
818 operating unit

DESCRIPTION OF THE PREFERRED EMBODIMENT

Figure 2:
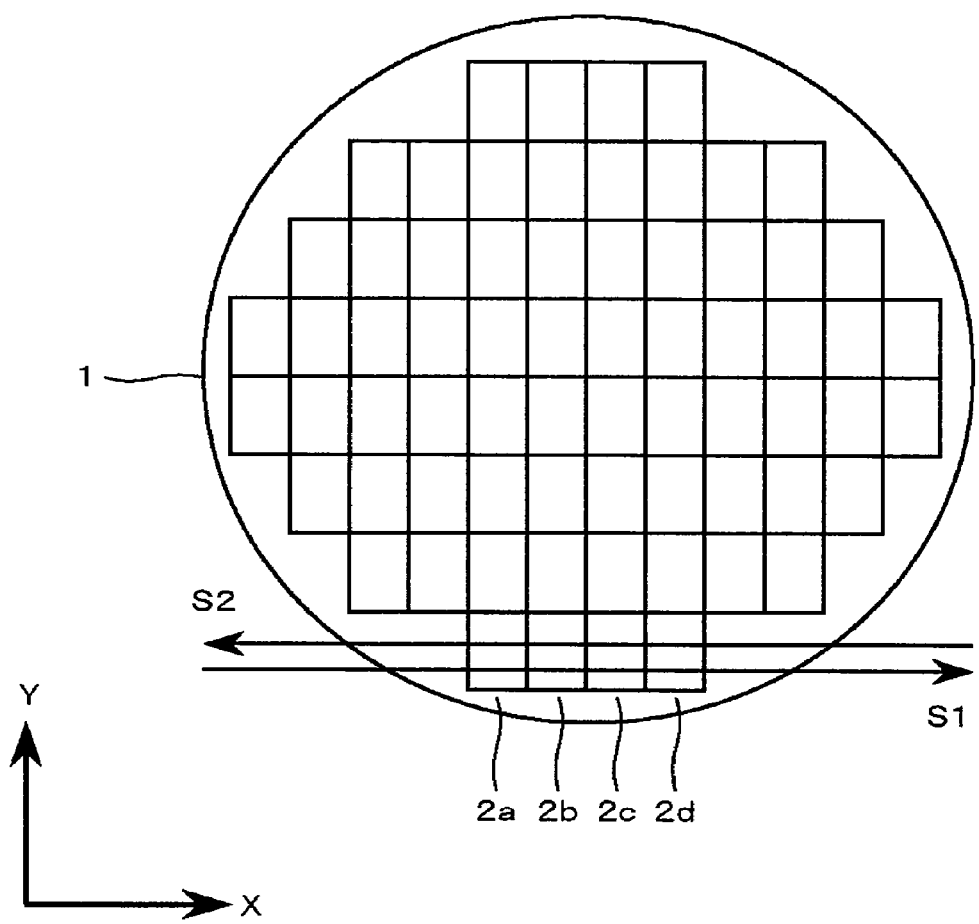
FIG. 2 is a diagram for explaining scanning of inspection light of the inspection apparatus as the first embodiment of the invention.

Embodiments of the invention will be described below with reference to the drawings
Device Configuration
FIG. 1 is a schematic diagram of an inspection apparatus as a first embodiment of the invention.
The inspection apparatus shown in FIG. 1 has illuminating means 10, detecting means 20, an X scale 30, a Y scale 40, and a processor 100. The inspection apparatus may further include an external computer 200. In the embodiment, the case of applying an optical inspection apparatus using a dark field image to the inspection apparatus of the invention will be described as an example.
Illuminating Means 10
The illuminating means 10 is a laser apparatus for generating inspection light such as a laser beam having a predetermined wavelength and irradiating the surface of a wafer 1 as an object to be inspected, with inspection light. For example, the surface of the wafer 1 may be obliquely irradiated with inspection light. The wafer 1 on which chips 2 are formed is mounted on at least an XY stage and can be moved at least in XY directions. By movement of the wafer stage in the X and Y directions, the surface of the wafer 1 is scanned with the inspection light emitted from the illuminating means 10.
FIG. 2 is a diagram for explaining scanning of inspection light of the inspection apparatus.
When the wafer stage on which the wafer 1 is mounted is moved in the X direction, inspection light emitted from the illuminating means 10 moves on the surfaces of chips 2a, 2b, 2c, and 2d formed on the wafer 1 in the direction shown by the arrow S1 to scan first line. Next, the wafer stage is moved in the Y direction. When the wafer stage is moved in the X direction opposite to that in the scan of the first line, the inspection light moves on the surfaces of the chips 2d, 2c, 2b, and 2a in the direction shown by the arrow S2 to scan the second line. By repeating the operations, the entire surface of the wafer 1 is scanned.
Detecting Means 20
Referring again to FIG. 1, inspection light emitted to the surface of the wafer 1 is scattered by a pattern or a defect in the surface of the wafer 1, so that scattered light is generated from the surface of the wafer 1. The detecting means 20 is, for example, a lens, a CCD, or a TDI, receives the scattered light generated on the surface of the wafer 1, converts the intensity of the light to an electric signal, and outputs the electric signal as an image signal to the processor 100.
X Scale 30 and Y Scale 40
The X scale 30 and the Y scale 40 are, for example, laser scales and the like, detect the position in the X direction and the position in the Y direction of the wafer stage on which the wafer 1 is mounted, and output the position information to the processor 100.
Processor 100
The processor 100 has an A/D converter 110, an image processor 120, a defect determining apparatus 130, a coordinate managing apparatus 140, an inspection result storage 150, an inspection result display device 160, an input device 170, and a result processor 180.
A/D Converter 110
The A/D converter 110 converts an analog image signal inputted from the detecting means 20 to a digital image signal and outputs the digital image signal.
Image Processor 120
The image processor 120 has an image comparing circuit 121, a threshold computing circuit 122, and a threshold storing circuit 123.
Image Comparing Circuit 121
The image comparing circuit has, for example, a delay circuit and a difference detection circuit and plays the role of comparing unit which compares an image signal of an inspection area detected by the detecting means 20 with an image signal of a corresponding pixel in a reference area and detecting the difference between the signals. The delay circuit receives an image signal from the A/D converter 110, delays it, and outputs an image signal of the inspection area already irradiated with inspection light immediately before the inspection area being presently irradiated with inspection light in the scan shown in FIG. 2. The difference detection circuit receives both an image signal of the inspection area being presently irradiated with inspection light from the A/D converter 110 and an image signal from the delay circuit, and detects and outputs the difference between the image signals. In such a manner, the image comparing circuit 121 compares the image signal in the inspection area and the image signal in the reference area adjacent to the inspection area. In the case where a defect exists in the surface of the inspection area, light scattered by the defect appears as the difference of image signals of adjacent chips.
The image comparing circuit 121 may have a memory that stores data of an image signal of a conforming chip prepared in place of the delay circuit, and perform comparison with the image signal of the inspection area of the conforming chip.
Threshold Computing Circuit 122
The threshold computing circuit 122 functions, for example, as threshold computing unit which computes a threshold to be compared with the difference of image signals of the corresponding pixels of the inspection area on the basis of statistics of image signals of corresponding pixels of inspection areas. That is, the threshold computing circuit 122 makes an image signal of the inspection area from the A/D converter 110 and an image signal of each of reference areas from the delay circuit correspond to each other on a pixel basis, calculates a variation (standard deviation) amount among the inspection areas, and calculates threshold data used for determination of the presence/absence of a defect on the basis of the variation amount.

The variation amount may be calculated by using a labeling process.

Threshold Storing Circuit 123

In the threshold storing circuit 123, a threshold inputted from the threshold computing circuit 122 is stored so as to be associated with coordinate information of an inspection area inputted from the coordinate managing apparatus 140.

Defect Determining Apparatus 130

The defect determining apparatus 130 has a determination circuit 131 and coefficient tables 132 and 133.

Coefficient Tables 132 and 133

In the coefficient tables 132 and 133, a coefficient for changing the threshold computed by the threshold computing circuit 122 is stored so as to be associated with coordinate information on a wafer. The coefficient tables 132 and 133 receive coordinate information from the coordinate managing apparatus 140 and output coefficients corresponding to the coordinate information to the determining circuit 131. When the coefficient stored in the coefficient tables 132 and 133 is outputted to the determination circuit 131, the threshold of corresponding coordinates is multiplied by the coefficient. Therefore, for example, in the case of inspecting a number of same products, a threshold is flexibly adjusted according to a place in an inspection area where a defect often occurs and a place on the wafer (near an edge or the like) on the basis of storage of past inspection/analysis data.

Determination Circuit 131

To the determination circuit 131, the difference signal between image signals of corresponding pixels in the inspection area and the reference area from the image comparing circuit 121, threshold data of the corresponding pixel read out from the threshold storing circuit 123, and coefficients for changing the threshold of the corresponding pixel, inputted from the coefficient tables 132 and 133 are entered.

The determination circuit 131 generates a threshold for determination by multiplying the threshold inputted from the image processor 120 by the coefficients of the corresponding pixel inputted from the coefficient tables 132 and 133. The determination circuit 131 compares the difference signal from the image comparing circuit 121 with the threshold for determination of the corresponding pixel and determines the presence/absence of a defect. In this case, when the difference signal is equal to or larger than the threshold for determination, the determination circuit 131 determines that the pixel is derived from light scattered by a defect and outputs the inspection result to the inspection result storage 150. The determination circuit 131 outputs the information of the threshold used for determination to the inspection result storage 150.

Coordinate Managing Apparatus 140

The coordinate managing apparatus 140 detects X and Y coordinates of a position on the wafer 1 presently irradiated with inspection light on the basis of position information of a wafer stage (that is, position information of the wafer 1) inputted from the X scale 30 and the Y scale 40, and outputs the coordinate information to the image processor 120, the defect determining apparatus 130, and the inspection result storage 150. The coordinate managing apparatus 140 also stores arrangement information of inspection areas on the wafer 1. Arrangement information of inspection areas stored in the coordinate managing apparatus 140 is outputted to the image processor 120 and the coefficient tables 132 and 133.

Inspection Result Storage 150

The inspection result storage 150 stores the inspection result inputted from the defect determining apparatus 130 and the coordinate information of the corresponding pixel inputted from the coordinate managing apparatus 140 so as to be associated with each other. The inspection result storage 150 also stores information of the threshold inputted from the defect determining apparatus 130 so as to be associated with the inspection result of the corresponding pixel or coordinate information.

Inspection Result Display Device 160

The inspection result display device 160 displays inspection result information inputted from the inspection result storage 150 and also displays a defect candidate image at the time of reviewing a defect candidate.

The inspection result display device 160 is an example of the display unit of the invention.

Input Device 170

For example, in the case of reviewing an inspection result, the input device 170 selects a defect candidate from a map of the inspection result display device 160 or enters a defect candidate number. Further, the input device 170 enters a result of determination of whether the defect candidate is a defect or a false defect.

The input device 170 is an example of the input unit of the invention.

Result Processor 180

The result processor 180 deletes a false defect group from a defect candidate group on the basis of a result of, for example, determination of whether the defect candidate in the input device 170 is a defect or a false defect. The result processor 180 computes a threshold at which the false defect group is not detected.

The result processor 180 is an example of the processor in the invention.

External Computer 200

The external computer 200 reviews a defect candidate off line from the inspection result of the inspection result storage 150 and generates the inspection condition data.

Inspection Condition Data Generating Procedure

An inspection condition data generating procedure of the inspection apparatus having the above-mentioned configuration will be described.

Figure 3:
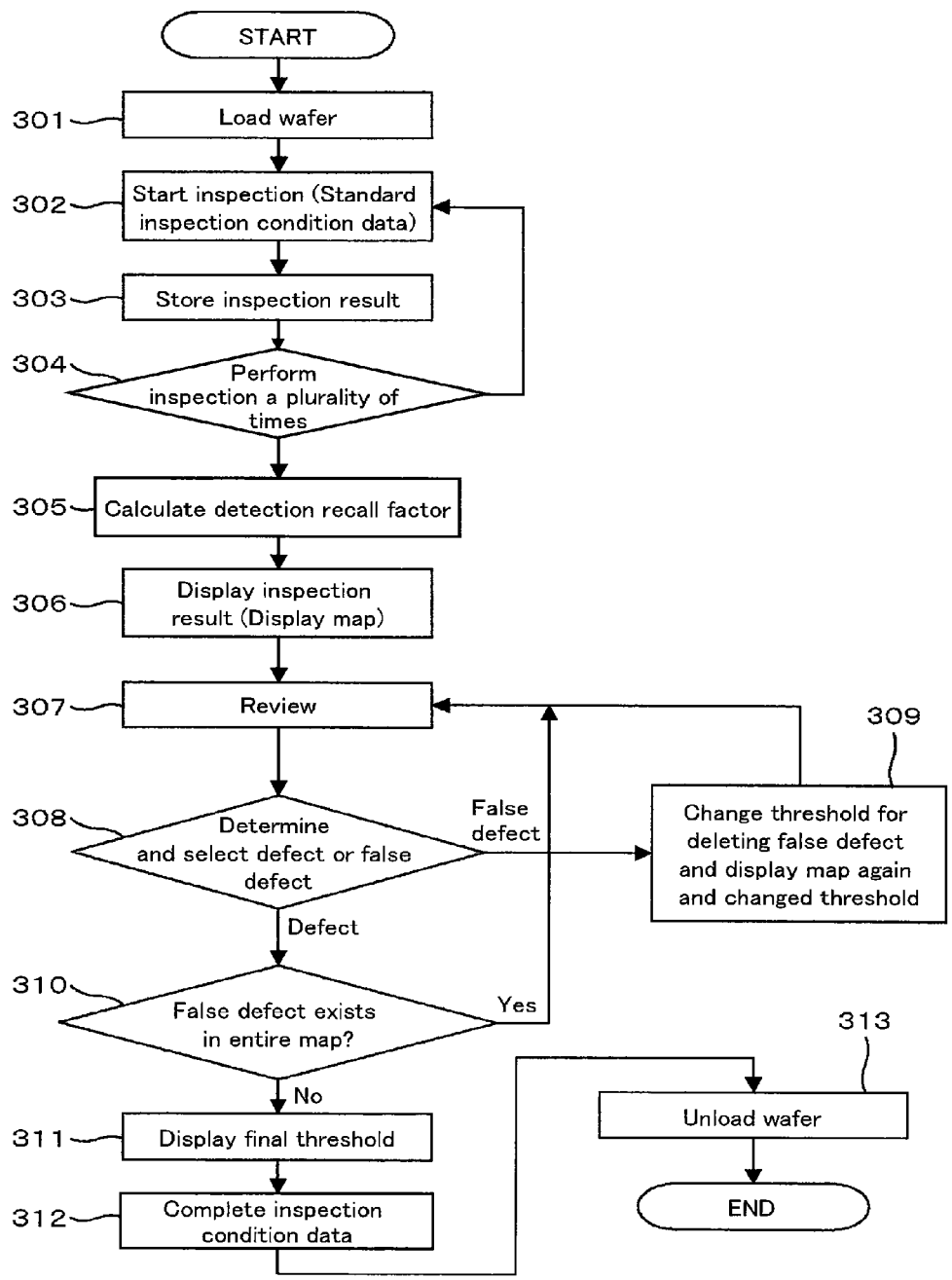
FIG. 3 is a flowchart of generation of inspection conditions of the inspection apparatus as the first embodiment of the invention.

FIG. 3 is a flowchart of generating inspection condition data.

First, at 301, a wafer is loaded on the inspection apparatus. Next, at 302, a wafer is inspected with standard inspection condition data. At 303, the inspection result is stored in the inspection result storage 150.

Each of the results detected in the inspection will be used as a defect candidate.

At 304, the inspection is repeated by designated number of inspection times under conditions almost the same as the above-mentioned inspection conditions, and inspection results are stored in the inspection result storage 150. The number of inspection times may be arbitrarily set.

At 305, results in which coordinates of defect candidates detected in the inspections are within a specific range are set as the same defect candidate. The recall factor of each of the defect candidates is computed by the following formula. The result is stored in the inspection result storage 150.

Detection recall factor(%)=(number of detection times/number of inspections)×100

It is highly possible that a defect candidate of low detection recall factor is a false defect caused by both variations in the sampling due to a stage coordinate error or the like, and electrical noise.

In the condition generating procedure, it is necessary to find a false defect from the defect candidate group and set a threshold at which the false defect is not detected. It is important to efficiently find a false defect in order to generate a measurement condition in short time. Therefore, by performing detection from the defect candidate group of the low recall factor, a false defect can be found efficiently.

At 306, the defect candidate group in the designated recall factor range is displayed in the inspection result display device 160.

Figure 4:
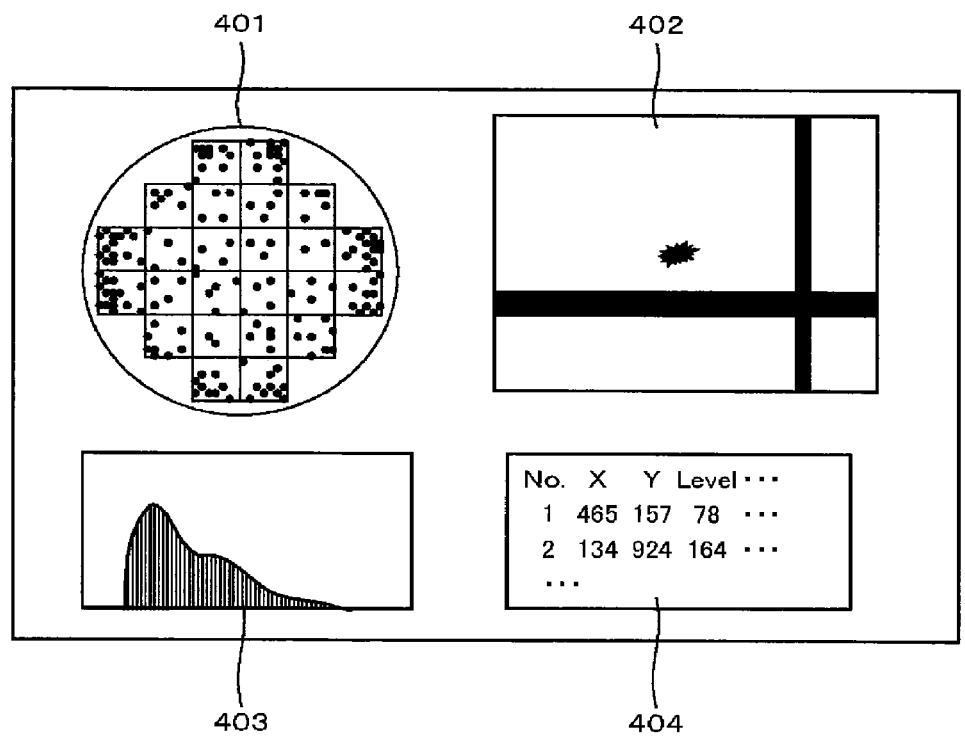
FIG. 4 is a diagram showing a display example of inspection results of the inspection apparatus as the first embodiment of the invention.

In FIG. 4, 401 denotes a wafer map diagram in which a defect candidate group is displayed on the map. 402 denotes a review screen for displaying an image of defect candidates (for example, an observation image obtained by a microscope). 403 shows a distribution of a defect candidate group. The horizontal axis denotes a characteristic quantity of the defect candidate group, and the vertical axis indicates frequency. The frequency expresses the distribution of the defect candidate group.

The characteristic quantity is a quantity depending on at least intensity of scattered light of the defect candidate. For example, a vertical-direction component of intensity of scattered light (the number of defect candidate detection pixels), the sum of the vertical-direction component of intensity of scattered light and a horizontal-direction component (total brightness of defect candidates), defect candidate total brightness/the number of defect candidate detection pixels, standard deviation of intensity of scattered light (defect candidate detection brightness/statistical threshold), defect candidate coordinates, or defect candidate detection recall factor is used.

Referring again to FIG. 3, at 307, a review is made to determine whether the defect candidate is a defect or a false defect. When a defect candidate on the wafer map diagram 401 is designated by mouse operation or the defect candidate number is entered with a keyboard, a defect candidate review image is displayed on the review screen 402. By selecting a defect candidate with low recall factor and low defect candidate detection brightness/statistical threshold, a false defect can be searched efficiently.

At 308, a user selects a defect or a false defect on the basis of the defect candidate review image.

The user determines whether the defect candidate is a defect or a false defect from the defect candidate image. When there is a defect in the defect candidate image, the user determines that the defect candidate is a defect. When there is no defect in the defect candidate image, the user determines that the defect candidate is a false defect.

When a false defect is selected, at 309, defect candidate groups having a characteristic quantity equal to or less than that of the false defect selected are classified from all of defect candidate groups. The classified defect candidate groups are handled as false defect groups and deleted from the map, or displayed in another sign. Further, a threshold is calculated from the characteristic quantity of the false defect group, and the calculated threshold is displayed. By deleting the defect candidate group handled as the false defect group from the map, the defect candidate group having the characteristic quantity which is equal to or less than that of the selected false defect is not reviewed, and the number of reviews can be reduced. By displaying the false defect group in another sign, history of defect candidates handled as false defects is visually shown.

Figure 5:
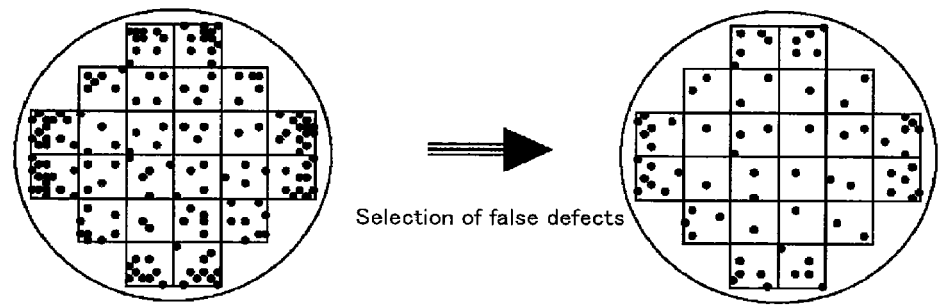
FIG. 5 is a diagram showing example of deletion of false defects after teaching of the false defect.
Figure 6:
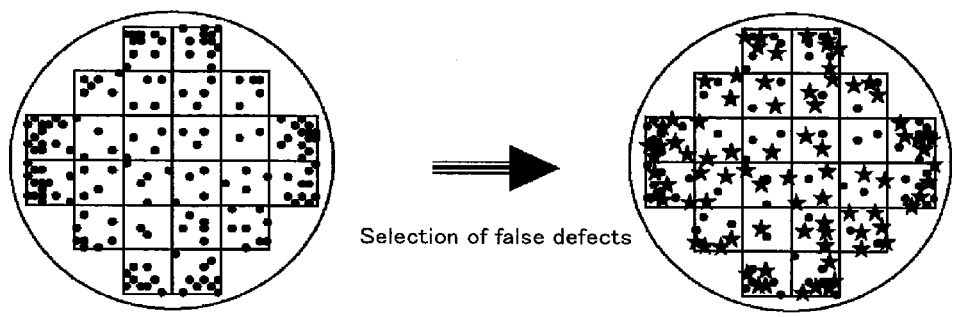
FIG. 6 is a diagram showing an example of displaying signs by false defects after the teaching of the false defect.

FIG. 5 shows an example of deleting a defect candidate group having a characteristic quantity equal to or less than that of the false defect from the map. FIG. 6 shows an example of displaying a defect candidate group having a characteristic quantity equal to or less than that of the false defect on the map by use of another sign.

Similarly, the review of the defect candidate at 307, selection of either a defect or a false defect at 308, and deletion of the defect candidate group having the characteristic quantity equal to or less than that of a false defect at 309 are repeated.

At 310, the presence or absence of a false defect in the entire map is determined. The 307, 308, and 309 are repeatedly performed until there is almost no false defect.

Figure 7:
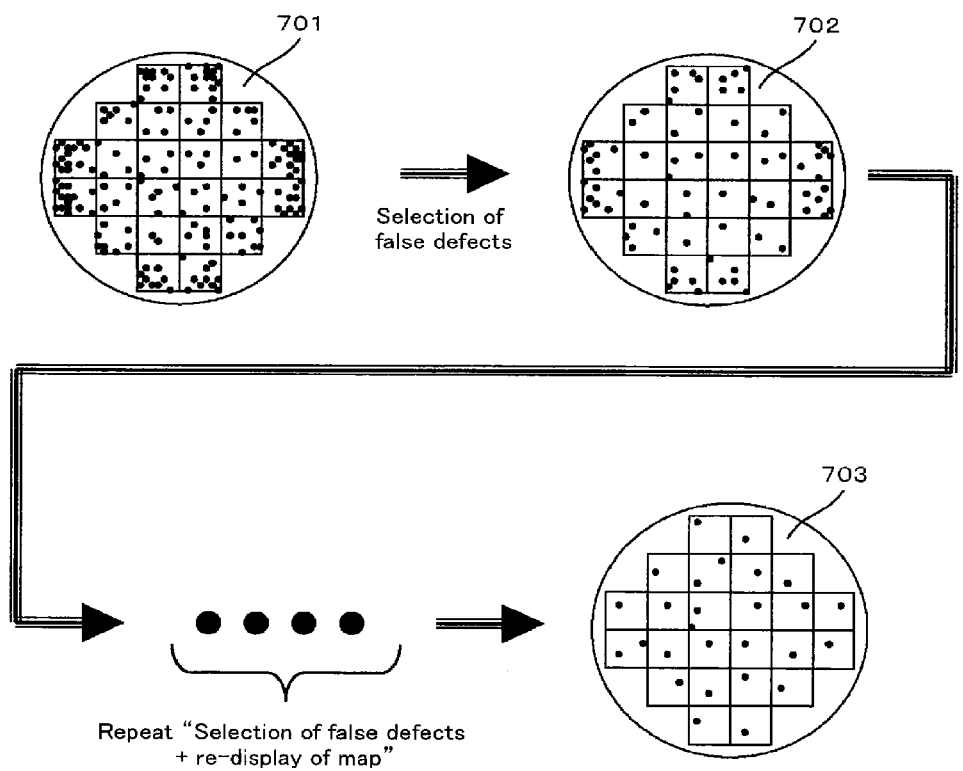
FIG. 7 is a diagram showing an example of a map change according to the teaching of the false defect.

FIG. 7 is a diagram showing the flow of the 307, 308, and 309 on the map.

The number 701 denotes a map showing a result of an inspection with standard inspection condition data. The number 702 denotes a map after the false defect selection is performed on the map 701. Further, selection of a false defect is repeated. Finally, the false defects are deleted from the map as shown in 703.

Referring again to FIG. 3, at 311, the threshold calculated from the characteristic quantity of the false defect is displayed and stored. The inspection condition data is completed at 312.

At 313, the wafer is unloaded, and the process is finished.

By performing the review as described above, the inspection condition data is tuned. In other words, "the review is the tuning of inspection condition data".

The invention is not limited to inspection of a semiconductor wafer but can be widely applied to inspections of a flaw, defect, dirt, or the like in the surfaces of various objects. For example, the invention can be applied to an appearance inspection, a liquid crystal inspection, and the like.

As an effect of the embodiment, by reviewing a defect candidate, selecting a defect or a false defect, and deleting defect candidates each having a characteristic quantity equal to or less than that of the false defect from the map or displaying the false defect in another sign, the false defects can be visually determined. Since the defect candidate having the characteristic quantity equal to or less than that of the selected false defect is deleted from the map or displayed in another sign, the defect candidates unnecessary for setting the threshold are not reviewed. Therefore, the number of defect candidates reviewed can be largely reduced as compared with the conventional case. Further, by repeating the above-mentioned work, the threshold is automatically calculated, and an inspection result map on the basis of the threshold is displayed. Thus, a re-inspection is unnecessary.

As a result, the inspection condition generation time can be reduced.

Second Embodiment

Figure 8:
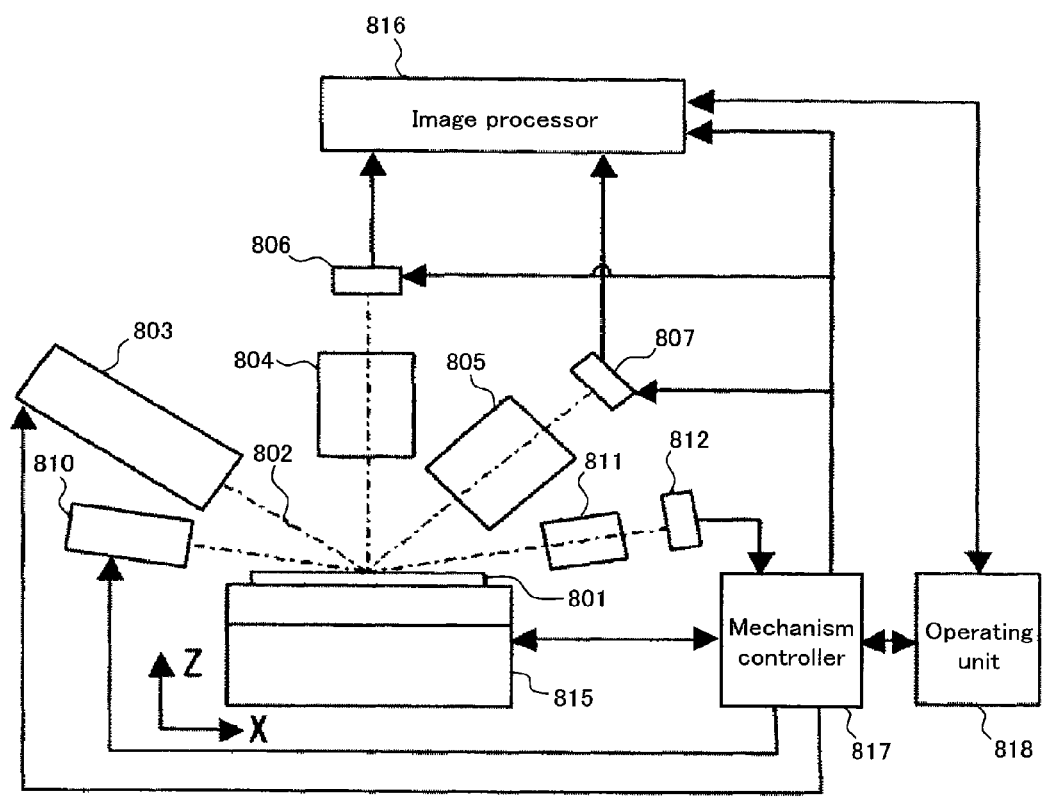
FIG. 8 is a general schematic configuration diagram of a defect inspection apparatus in a second embodiment of the invention.

FIG. 8 is a general schematic configuration diagram of a defect inspection apparatus to which the invention is applied. In FIG. 8, a sample 801 (a semiconductor wafer, a display device, a printed board, or the like) as an object to be inspected is mounted on a stage 815. The stage 815 is, for example, a combination of an XY stage, a Z stage, a θ stage, and the like.

An apparatus capable of scanning the sample 801 in the XY plane is employed so that the entire surface of the sample 801 can be inspected by inspection optical systems 804 and 805 disposed above the stage 815. The sample 801 is irradiated with illumination light 802 emitted from an illumination optical system 803 (including a light source). Light incident on the inspection optical systems 804 and 805 disposed above the sample 801, of scattered reflection light from a defect such as a pattern, a particle, and the like on the sample 801 is led to sensors 806 and 807, photoelectrically converted, and transmitted as an image signal to an image processor 816.

The inspection optical systems 804 and 805 may have analyzers. As the sensors 806 and 807, linear CCD sensors, TDI sensors, or the like are used. In the image processor 816, an image is formed from the transmitted image signal, images from neighboring same patterns are compared with each other, and a defect is detected from the obtained difference.

The defect inspection apparatus has an auto focusing (AF) system. The AF system comprises an illuminating system 810, a photosensitive system 811, and an AF sensor 812. At the time of scanning a sample, the AF system detects a change in the sample height (out of focus) and feeds it back to a mechanism controller 817 so that an image obtained by the sensors 806 and 807 is not blurred.

By an operating unit 818, a control of the mechanism controller 817, an image process of the image processor 816, and the like are instructed.

Figure 9:
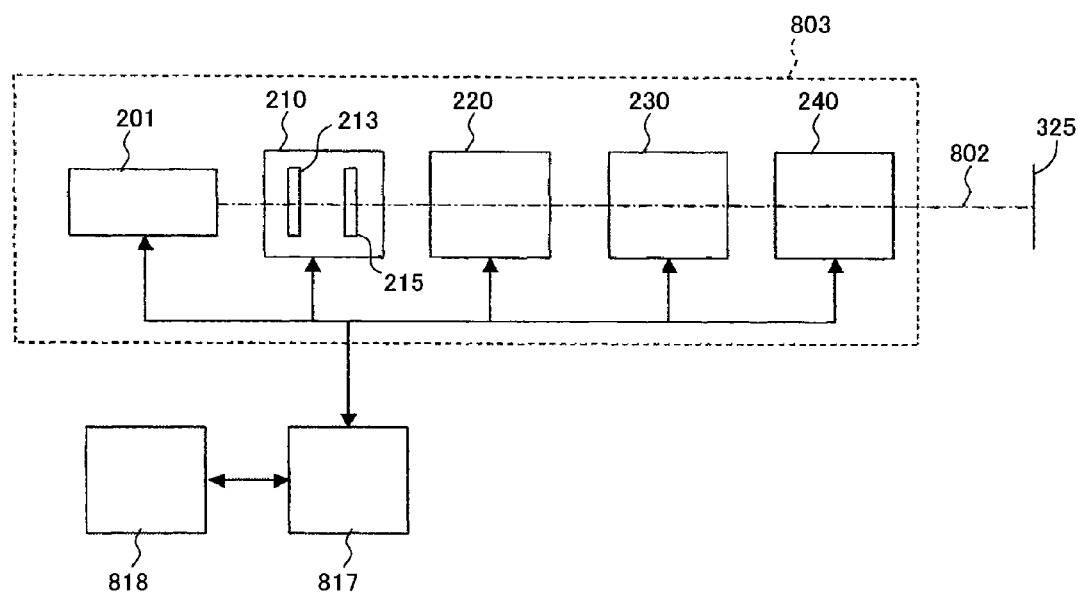
FIG. 9 is a diagram showing a schematic configuration of an illustration optical system the defect inspection apparatus in the second embodiment of the invention.

FIG. 9 is a diagram showing a schematic configuration of the illumination optical system 803 in the defect inspection apparatus shown in FIG. 8. In FIG. 9, light emitted from a light source 201 passes through a polarization light adjuster 210, a beam expander 220, a lens 230, and an elevation angle switching mirror 240 and reaches an illumination region 325 on the sample 801. As the light source 201, for example, a laser for emitting light in a linearly-polarized state is used. The polarization light adjuster 210 includes, for example, a half-wavelength plate 213, a quarter-wavelength plate 215, and a rotation driving mechanism for the plates. The operations of the light source 201, the polarization light adjuster 210, the beam expander 220, the lens 230, and the elevation angle switching mirror 240 are controlled by the mechanism controller 817.

In the illumination optical system 803, the polarization direction of linearly-polarized light emitted from the light source 201 is set to a direction deviated from the s-polarized light or p-polarized light in accordance with the direction or pitch of the pattern on the sample 801 and the illumination elevation angle (or incidence angle) of the illumination light 802. Depending on the characteristics of a sample, elliptically-polarized light may be used as the polarized light of illumination.

Light whose polarization state has been adjusted by the polarization light adjuster 210 is expanded to a required size by the beam expander 220 and the resultant light is emitted to the lens 230. As the lens 230, a cylindrical lens is used. The light passed through the cylindrical lens (lens 230) is adjusted by the elevation angle switching mirror 240 so that the illumination elevation (or incidence angle) becomes a predetermined angle. After that, the light is emitted onto the surface of the sample 801. The illumination region 325 becomes linear.

Figure 10A:
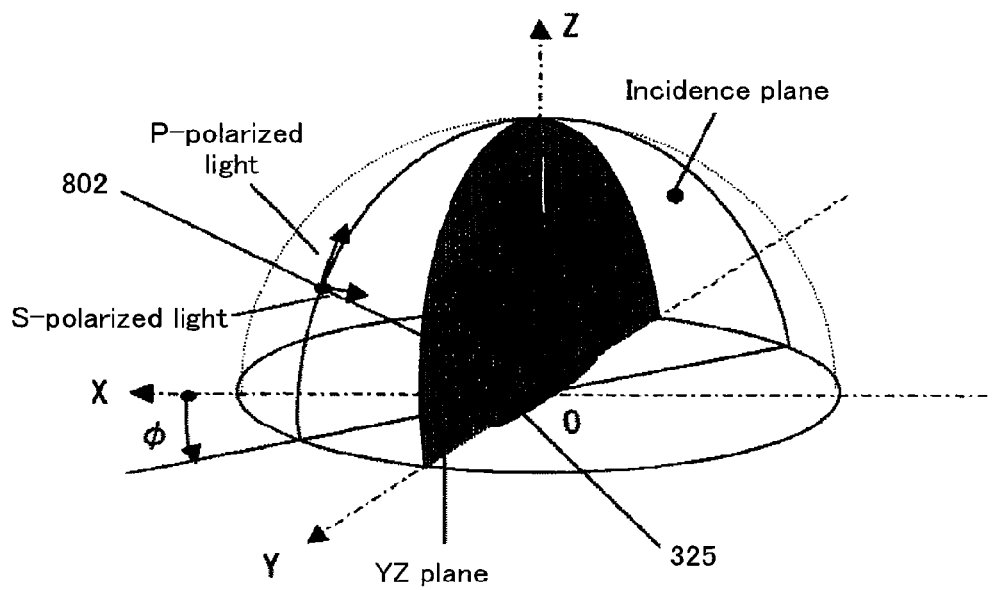
FIGS. 10A and 10B are diagrams showing an example of setting a polarization direction of a beam to be applied to a sample in the second embodiment of the invention.
Figure 10B:
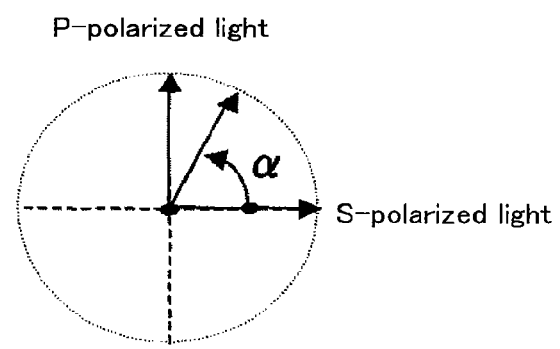

FIGS. 10A and 10B are diagrams showing an example of setting the polarization direction of a beam emitted to the sample 801 in the second embodiment of the invention.

In FIG. 10A, the surface of the sample 801 is set as an xy plane, and the direction normal to the surface of the sample 801 is set as a z direction. It is assumed that the illumination region 325 is a region on a straight line along the y axis and the origin is in the center of the region. When the incidence azimuth angle of light projected on the xy plane is ϕ, the incidence angle of light is θ (therefore, the elevation angle is 90−θ), and the illumination light (axis) is 802, the p-polarized light direction and the s-polarized light direction of the illumination light 802 are as shown in FIGS. 10A and 10B. In the second embodiment of the invention, illumination light having a polarization vector in a direction turned by a degrees from the direction of the s-polarized light as a reference is used.

It is assumed that the polarization vector in the direction of azimuth a degrees is a vector "a", a unit vector in the s-polarized light direction is a vector "s", and a unit vector in the p-polarized light direction is a vector "p". The vector "a" can be expressed as the following equation (1).

$$\vec{a} = (a_x, a_y, a_z) = \cos\alpha \vec{s} + \sin\alpha \vec{p} \qquad \text{Equation (1)}$$

When the unit vector in the travel direction of the illumination light 802 is a vector "r", the vector "r" can be expressed by the following equation (2).

$$\vec{r} = (-\sin\theta\cos\phi, -\sin\theta\sin\phi, -\cos\theta) \qquad \text{Equation (2)}$$

The vector "s" can be expressed by the following equation (3), and the vector "p" can be expressed by the following equation (4).

$$\vec{s} = (-\sin\phi, \cos\phi, 0) \qquad \text{Equation (3)}$$

$$\vec{p} = \vec{s} \times \vec{r} = (-\cos\phi\cos\theta, -\sin\phi\cos\theta, \sin\theta) \qquad \text{Equation (4)}$$

Therefore, the vector "a" (ax, ay, and az) can be expressed by the following equations (5), (6), and (7).

$$a_x = -\cos\alpha\sin\phi - \sin\alpha\cos\theta\cos\phi \qquad \text{Equation (5)}$$
$$= \sqrt{\cos^2\theta\cos^2\phi + \sin^2\phi} \times \sin(\alpha + \beta)$$
$$\tan\beta = \frac{\tan\phi}{\cos\theta}$$

$$a_y = \cos\alpha\cos\phi - \sin\alpha\cos\theta\sin\phi \qquad \text{Equation (6)}$$
$$= \sqrt{\cos^2\theta\sin^2\phi + \cos^2\phi} \times \sin(\alpha + \beta')$$
$$\tan\beta' = \frac{-1}{\cos\theta\tan\phi}$$

$$a_z = \sin\alpha \sin\theta \qquad \text{Equation (7)}$$

Figure 11:
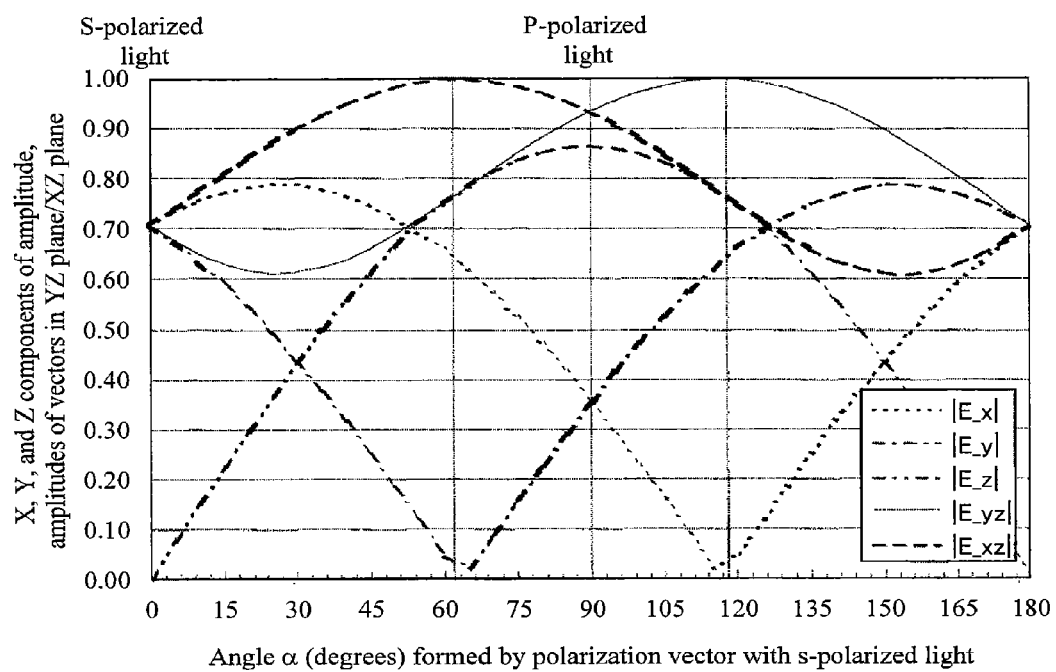
FIG. 11 is a diagram showing an example of a calculation result by setting polarization of illumination light in the second embodiment of the invention.

FIG. 11 shows an example of calculating amplitude components of electric field of light incident on the sample 801 in the case of using linearly-polarized light of azimuth a degrees as the illumination light 802, in accordance with the calculation formulae (5) to (7) as polarized state calculation formulae. The example shown in FIG. 11 relates to the case where the incident azimuth angle ϕ of the illumination light 802 projected on the xy plane is 45 degrees and the incident angle of the illumination light 802 is 60 degrees (that is, the elevation is 30 degrees).

In FIG. 11, the vertical axis denotes the amplitude of a vector, and the horizontal axis indicates angle α formed by the vector and s-polarized light. The dotted line shows a component in the x direction of electric field. The dashed-dotted line shows a component in the y direction of the electric field. The dashed-two dotted line indicates a component in the z direction of the electric field. The solid line indicates a vector in the yz plane of the electric field. The broken line indicates a vector in the xz plane of the electric field.

It is known from FIG. 11 that the components x, y, and z of the electric field largely change according to the value of the angle α. The component "z" of the electric field becomes the minimum in the case of the s-polarized light and becomes the maximum in the case of the p-polarized light. The components "x" and "y" become the minimum under the condition between the s-polarized light and the p-polarized light, that is, the condition that α=−β, or α=−β' on the basis of the equation (5) or (6). The components "x" and "y" become the maximum under the condition that α=−β+90 degrees, or α=−β'+90 degrees.

There is, consequently, the possibility that an optimum polarization condition for defect detection exists between the s-polarized light and the p-polarized light in relation to the pattern on the sample 801.

Figure 12A:
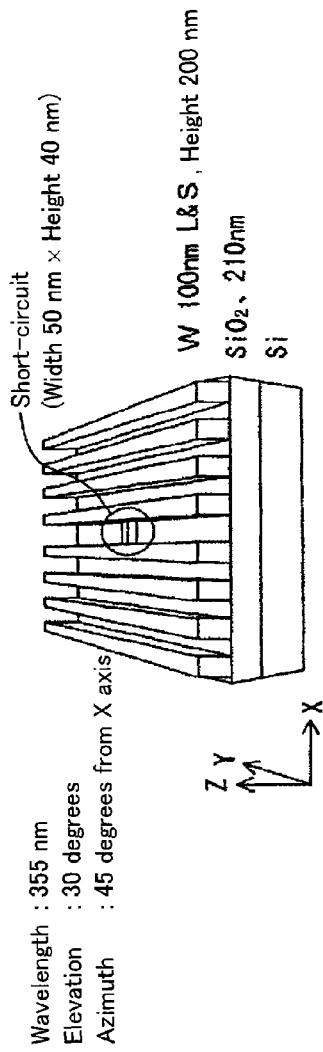
FIGS. 12A and 12B are diagrams showing an example of a simulation result of an effect on detection of a short-circuit defect of linearly-polarized light of azimuth ( ) degrees in the second embodiment of the invention.
Figure 12B:
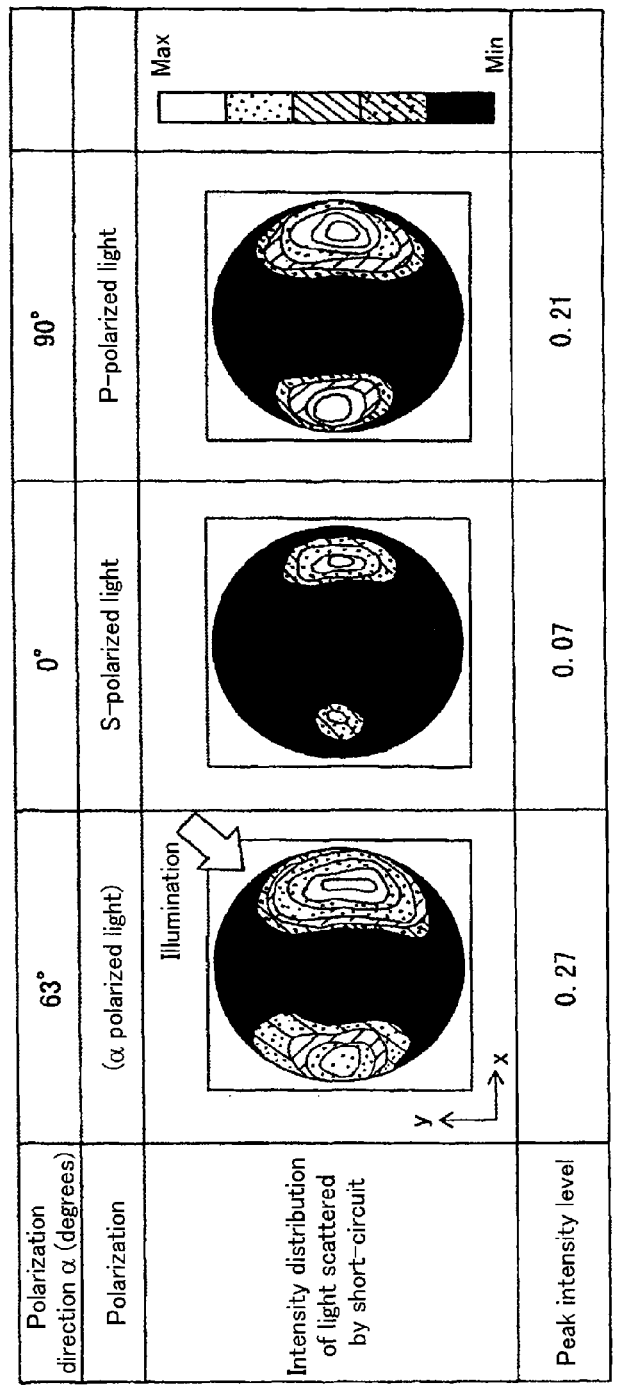

FIGS. 12A and 12B are diagrams showing an example of a simulation result of effects of linearly-polarized illumination of the azimuth a degrees upon detection of a short-circuit defect.

FIG. 12A shows a model of a pattern and a defect on the sample 801. FIG. 12B is a diagram of distributions, viewed from above, of light scattered by the defect used for the model shown in FIG. 12A by simulation.

The model of the defect used in the example is a short-circuited part in the bottom of a trench in wiring (film thickness of 200 nm) of tungsten of 100 nm-lines and spaces further formed on an oxide film (thickness of 210 nm) formed on the silicon substrate. The width of the short-circuited part is 50 nm, and the height is 40 nm.

FIG. 12B shows scattered light distributions in the case where illumination light having a wavelength of 355 nm is emitted to the defect model at an incidence angle θ of 60 degrees (therefore, the elevation is 30 degrees) from a direction of the azimuth angle of 45 degrees. The scattered light distributions are normalized with their respective peak intensity levels which are written in the lowest row.

As shown in FIG. 12B, when the α is set to 63 degrees, the scattered light level (peak intensity level 0.27) is obtained, which is higher than that (peak intensity level 0.21) in the case of the p-polarized light by about thirty percent.

It corresponds with the condition that the component "y" in the electric field in the result obtained by the computation formula becomes zero, that is, the electric field exists in the xz plane in FIG. 11 as described earlier.

It is understood that, by selecting a proper value as the azimuth a degrees as described above, the short-circuit defect can be detected at higher sensitivity.

In reality, a rotational angle α adapted to detect a short-circuit in a circuit pattern on a sample depends on the direction of a major straight line group in the circuit pattern on the sample, the cycles of the straight lines in the group, the azimuth angle φ and the incidence angle θ of the illumination light 802, and the like. Consequently, the rotational angle has to be set in accordance with those conditions and by use of the formulae (1) to (7).

The formulae (1) to (7) are stored in the storage of the mechanism controller 817. Necessary conditions are inputted from the operating unit 818 to the mechanism controller 817. The mechanism controller 817 executes the formulae (1) to (7) in accordance with the inputted conditions and controls the illumination optical system 803 so that the rotational angle becomes the obtained angle α.

As described above, in the second embodiment of the invention, the polarization a of light emitted to a sample as an object subject to defect detection (the angle α from the s-polarized light) is calculated by substituting the conditions of the circuit pattern of the sample 801 and the azimuth angle and the incidence angle of illumination light into the predetermined formulae (5) to (7). The polarization a lies between the p-polarized light and the s-polarized light. By irradiating the sample 801 with the calculated polarization a light, a defect is inspected. Consequently, the defect inspection method and apparatus having improved inspection sensitivity of an inspection on a short-circuit at the bottom between neighboring wires and capable of detecting even a pattern short-circuit at the bottom between a plurality of wires arranged in parallel in a finely formed pattern can be realized.

In the second embodiment of the invention, the case of using linearly-polarized light as illumination light and turning the azimuth from the s-polarized light by a degrees has been described as an example. It is also possible to give a phase difference between the s-polarized light direction component and p-polarized light direction component of polarized light turned by a degrees so as to make polarized light which is emitted as a result, into elliptically-polarized light. In such a manner, peculiarities in diffracted light from the pattern are reduced and, in some cases, a defect can be easily detected.

Third Embodiment

Figure 13A:
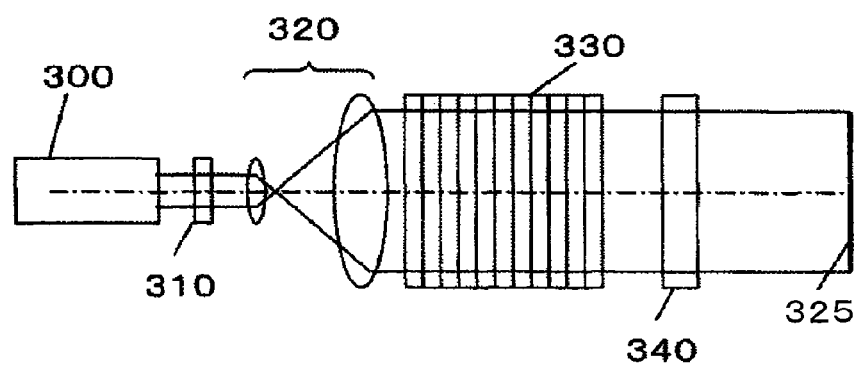
FIGS. 13A and 13B are schematic configuration diagrams of an illumination optical system 803 of a defect inspection apparatus in a third embodiment of the invention.
Figure 13B:
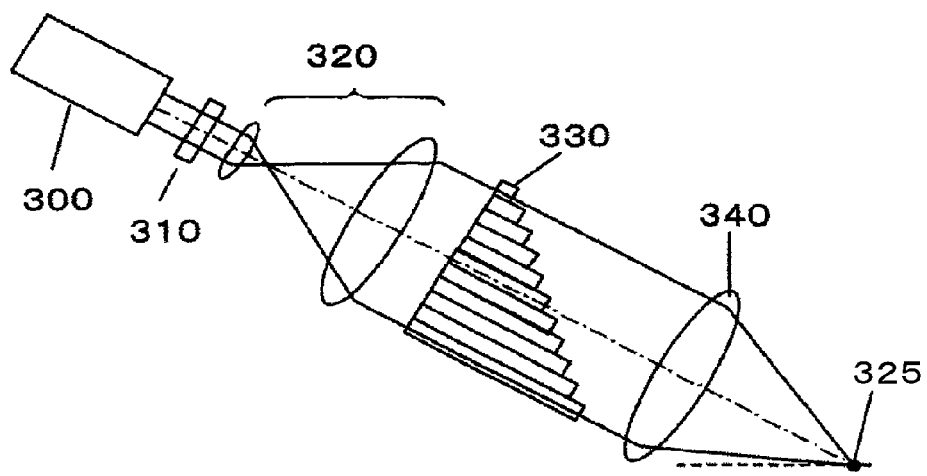

FIGS. 13A and 13B are schematic configuration diagrams of the illumination optical system 803 of the defect inspection apparatus in a third embodiment of the invention. Since the general configuration of the defect inspection apparatus is similar to that of the example shown in FIG. 8, it will not be shown and its description will not be repeated.

In FIGS. 13A and 13B, a beam (coherent light) of illumination light of linearly-polarized light or elliptically-polarized light emitted from a light source 300 passes through a depolarizer 310, and is expanded by a beam expander 320. The expanded beam enters multiple glass block element 330. The light passed through the multiple glass block element 330 is condensed on a straight line by a cylindrical lens 340, and the condensed light reaches the illumination region 325 on the surface of the sample 801.

As the depolarizer 310, for example, a birefringent substrate made of crystal or the like which is processed in a wedge form, or a wedge-shaped transparent substrate having no birefringent property, which is adhered thereto, is used.

By making the phase difference given to the polarized-light components of two directions orthogonal to each other vary according to the position where a beam passes, the polarization state of the entire passing beam can be changed to a mixed state of various polarization states (the polarization is disturbed or the polarization state is cancelled).

In the third embodiment of the invention, by expanding a beam having a polarization state which varies according to a position in the beam and making the beam pass through the multiple glass block element 330, the optical path difference which varies according to positions is given. The multiple glass block element 330 is a row of glass block elements having different lengths, and gives an optical path difference exceeding coherence length between neighboring blocks. In such a manner, light passed through the multiple glass block elements 330 becomes a slit-like beam group in different polarization states without interfering each other depending on their positions. The beam group is condensed by the cylindrical lens 340, and emitted to the surface of the sample 801.

With such illumination light, images obtained through the inspection optical systems 804 and 805 (shown in FIG. 8) by the sensors 806 and 807 have a smoother gradation characteristic also in a pattern portion of low repeatability by the effect of averaging of peculiarities depending on polarization. Therefore, a noise component in an image is reduced, and defect detection sensitivity can be increased.

That is, also in the third embodiment of the invention, the defect inspection method and apparatus having improved inspection sensitivity of an inspection on a short-circuit at the bottom between neighboring wires and capable of detecting even a pattern short-circuit at the bottom between a plurality of wires arranged in parallel in a finely formed pattern can be realized.

Specifically, in the conventional technique, in an inspection of a pattern portion of low repeatability, a method of overlapping illumination light at different incidence angles, the coherency of which is reduced by providing optical path differences, is employed. However, a sufficient noise reduction effect cannot be obtained.

In contrast, in the third embodiment of the invention, the effect of reducing polarization dependency is also added, and a sufficient noise reduction effect can be obtained.

In the third embodiment of the invention, an example of combination of the depolarizer 310 and the multiple glass block element 330 has been described. However, the multiple glass block element 330 is not always necessary. In the case of omitting the multiple glass block element 330, the coherence reduction effect cannot be obtained but an effect of averaging the polarization dependency is obtained, so that the defect detection sensitivity can be increased.

Fourth Embodiment

Figure 14A:
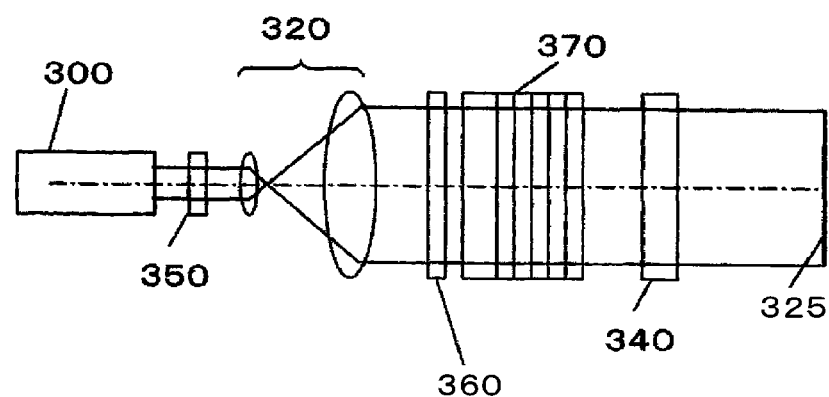
FIGS. 14A and 14B are schematic configuration diagrams of the illumination optical system 803 of a defect inspection apparatus in a fourth embodiment of the invention.
Figure 14B:
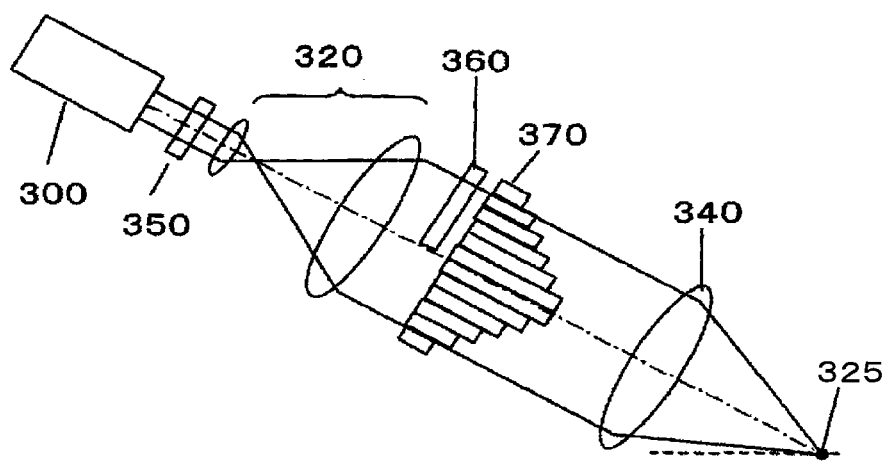

FIGS. 14A and 14B are schematic configuration diagrams of the illumination optical system 803 of the defect inspection apparatus in a fourth embodiment of the invention. Since the general configuration of the defect inspection apparatus is similar to that of the example shown in FIG. 8, it will not be shown and its description will not be repeated.

In the fourth embodiment of the invention, a beam of illumination light of linearly-polarized light or elliptically-polarized light emitted from the light source 300 passes through a half-wavelength plate 350 and is expanded by the beam expander 320. The expanded beam passes through a half-wavelength plate 360 provided in a region of about the half of the aperture. The beam passed through the half-wavelength plate 360 is incident on multiple glass block element 370. The beam passed through the multiple glass block element 370 is condensed on a straight line by the cylindrical lens 340, and the condensed light reaches the illumination region 325 on the surface of the sample 801.

In the fourth embodiment of the invention, the multiple glass block element 370 is formed in a shape almost symmetrical with respect to the optical axis of the illumination light as a center, and the half-wavelength plate 360 is provided so that the polarization state of light incident on the half region of the multiple glass block element 370 is orthogonal to that of polarized light incident on the other half region.

For example, a setting can be made as follows. In the case where linearly-polarized light is emitted from the light source 300, as shown in FIG. 14B, illumination light from the upper-half region of the multiple glass block element 370 corresponding to the region in which the half-wavelength plate 360 is disposed is p-polarized light, and illumination light from the lower-half region is s-polarized light.

By an inspection performed by irradiating a sample surface with illumination light in which the p-polarized light and the s-polarized light are mixed, the polarization dependency of vision of the pattern on the sample 801 is reduced, and noise of an image is reduced. As a result, sensitivity of a defect inspection can be improved.

That is, also in the fourth embodiment of the invention, the defect inspection method and apparatus having improved inspection sensitivity of an inspection on a short-circuit at the bottom between neighboring wires and capable of detecting even a pattern short-circuit at the bottom between a plurality of wires arranged in parallel in a finely formed pattern can be realized.

By turning the polarized light by 90 degrees by the half-wavelength plate 350 in the state shown in the diagrams, the illumination light in the upper half region can be switched to the s-polarized light, and the illumination light in the lower half region can be switched to the p-polarized light. By combining inspection images of both of the illumination states, noise of an image can be further reduced.

Further, in the fourth embodiment of the invention, in a manner similar to the third embodiment, image noise of the pattern portion of low repeatability is reduced, and defect detection sensitivity can be improved.

Although not shown, by adding a quarter-wavelength plate after the half-wavelength plate 350, clockwise circularly-polarized light and counterclockwise circularly-polarized light can be also combined. Also by combining the polarized light having a mathematical orthogonal relation, a similar effect of reducing noise in an inspection image can be expected.

Fifth Embodiment

Figure 15A:
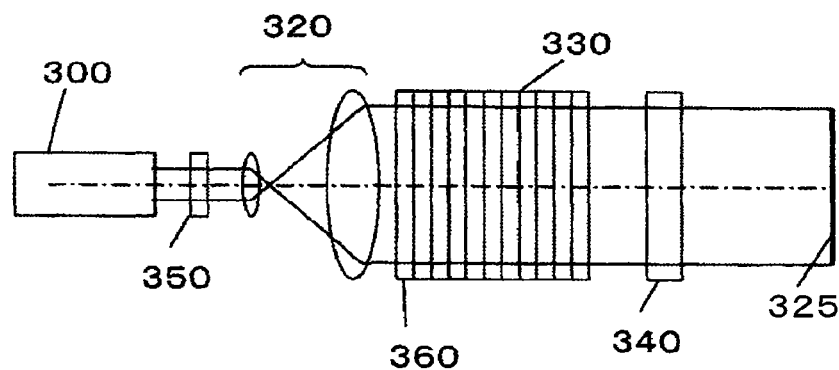
FIGS. 15A and 15B are schematic configuration diagrams of the illumination optical system 803 of a defect inspection apparatus in a fifth embodiment of the invention.
Figure 15B:
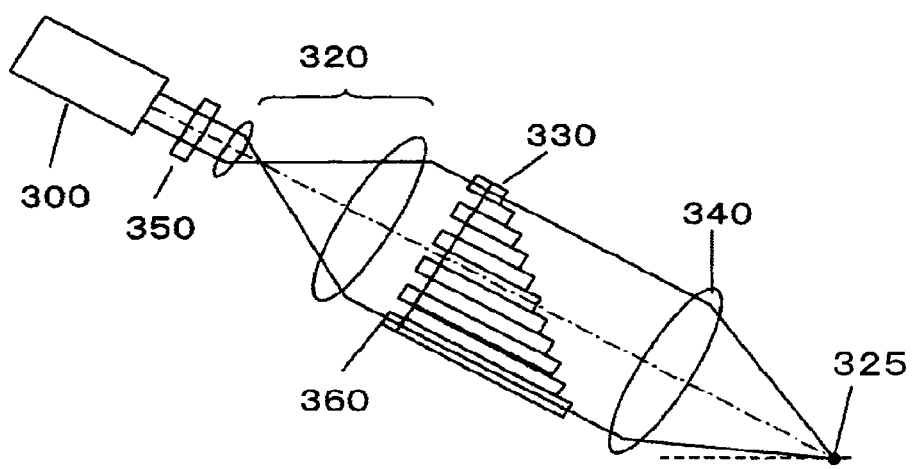

FIGS. 15A and 15B are schematic configuration diagrams of the illumination optical system 803 of the defect inspection apparatus in a fifth embodiment of the invention. Since the general configuration of the defect inspection apparatus is similar to that of the example shown in FIG. 8, it will not be shown and its description will not be repeated.

In the fifth embodiment of the invention, a beam of illumination light of linearly-polarized light or elliptically-polarized light emitted from the light source 300 passes through the half-wavelength plate 350 and is expanded by the beam expander 320. The expanded beam passes through the multiple glass block element 330. The half-wavelength plate 360 is provided every other block in the aperture on the incidence side of the multiple glass block element 330. The beam passed through the multiple glass block element 330 is condensed on a straight line by the cylindrical lens 340, and the condensed light reaches the illumination region 325 on the surface of the sample 801.

In the fifth embodiment of the invention, the polarization states of light emitted from the neighboring slit-like apertures of the multiple glass block element 330 are orthogonal to each other. For example, a setting can be made as follows. In the case where linearly-polarized light is emitted from the light source 300, as shown in FIG. 15B, illumination light from every other region of the multiple glass block element 330 is p-polarized light, and illumination light from the other regions is s-polarized light.

By an inspection with illumination light in which the p-polarized light and the s-polarized light are mixed, the polarization dependency of vision of the pattern is reduced, and noise of an image is reduced. As a result, sensitivity of a defect inspection can be improved.

By turning the polarized light by 90 degrees by the half-wavelength plate 350 in this state, the illumination light can be switched to the s-polarized light and the p-polarized light. By combining inspection images of both of the illumination states, noise of an image can be further reduced.

Also in the fifth embodiment of the invention, the defect inspection method and apparatus having improved inspection sensitivity of an inspection on a short-circuit at the bottom between neighboring wires and capable of detecting even a pattern short-circuit at the bottom between a plurality of wires arranged in parallel in a finely formed pattern can be realized.

Further, in the fifth embodiment of the invention, in a manner similar to the third embodiment, image noise of the pattern portion of low repeatability is reduced, and defect detection sensitivity can be improved.

What is claimed is:
1. An inspection apparatus comprising:
   an illumination optical system which illuminates an object with light;
   a detection optical system which detects light from the object;

a display system which displays a defect candidate group so as to correspond to coordinates on the object, based on a detection result from the detection optical system;

an input system for selecting a defect candidate having an arbitrary detection recall factor from the defect candidate group displayed on the display system; and a processing system programmed to perform the process functions of:

i) in the case where an arbitrary defect candidate selected from the defect candidate group by the input system is determined as a false defect, classifying the defect candidate group into a defect or false defect based on a detection recall factor of the determined false defect; and ii) obtaining a threshold for determining whether there is a defect on the object based on the classification result, wherein the display system is configured to reflect the classification result, and the input system is capable of selecting a plurality of arbitrary defect candidates on the display system.

2. The inspection apparatus according to claim 1, wherein the display system is configured to delete from the displayed object a defect candidate which is classified into the false defect in the classification.

3. The inspection apparatus according to claim 1, wherein the display system is configured to display a defect candidate which is classified into the false defect in the classification and a defect candidate which is classified into the defect in the classification in different signs on the displayed object.

4. The inspection apparatus according to claim 1, wherein the display system is configured to display distribution of the defect candidate group.

5. A method for setting a condition for inspection, the method comprising steps of:

illuminating an object with light;

detecting light from the object;

selecting a plurality of defect candidates having an arbitrary detection recall factor from a display screen which displays a defect candidate group so as to correspond to coordinates on the object;

each time the defect candidate is determined as a false defect, obtaining a position on the object of a defect to be classified and a position on the object of the false defect based on a detection recall factor of the determined false defect; and obtaining a threshold for inspection from the classification result.

6. The method according to claim 5, further comprising the step of:

obtaining the threshold which is updated each time the false defect is determined.

* * * * *